United States Patent
Sawaguchi et al.

(10) Patent No.: US 12,390,180 B2
(45) Date of Patent: Aug. 19, 2025

(54) DYNAMIC ANALYSIS DEVICE AND STORAGE MEDIUM

(71) Applicant: Konica Minolta, Inc., Tokyo (JP)

(72) Inventors: Toi Sawaguchi, Tokyo (JP); Ichirou Hamamoto, Fuchu (JP)

(73) Assignee: KONICA MINOLTA, INC., Tokyo (JP)

( * ) Notice: Subject to any disclaimer, the term of this patent is extended or adjusted under 35 U.S.C. 154(b) by 388 days.

(21) Appl. No.: 17/701,967

(22) Filed: Mar. 23, 2022

(65) Prior Publication Data

US 2022/0304642 A1 Sep. 29, 2022

(30) Foreign Application Priority Data

Mar. 23, 2021 (JP) ................................. 2021-048748

(51) Int. Cl.
*A61B 6/00* (2024.01)
*A61B 6/46* (2024.01)
*A61B 6/50* (2024.01)

(52) U.S. Cl.
CPC .............. *A61B 6/486* (2013.01); *A61B 6/463* (2013.01); *A61B 6/465* (2013.01); *A61B 6/504* (2013.01)

(58) Field of Classification Search
CPC ......... A61B 6/486; A61B 6/463; A61B 6/465; A61B 6/504
See application file for complete search history.

(56) References Cited

U.S. PATENT DOCUMENTS

| | | | | |
|---|---|---|---|---|
| 2013/0111387 | A1* | 5/2013 | Li | G16H 10/60 715/771 |
| 2015/0065817 | A1* | 3/2015 | Noji | A61B 6/5264 600/407 |
| 2019/0180440 | A1* | 6/2019 | Matsumoto | G06T 7/0016 |
| 2019/0298290 | A1* | 10/2019 | Noji | A61B 6/488 |

(Continued)

FOREIGN PATENT DOCUMENTS

| | | |
|---|---|---|
| JP | 2017205187 A | 11/2017 |
| JP | 2020081280 A | 6/2020 |
| WO | 2017017985 A1 | 2/2017 |

OTHER PUBLICATIONS

JPO Notice of Reasons for Refusal for corresponding JP Application No. 2021-048748; Issued Sep. 10, 2024.

(Continued)

*Primary Examiner* — Utpal D Shah
(74) *Attorney, Agent, or Firm* — CANTOR COLBURN LLP (57) ABSTRACT

Provided is a dynamic analysis device that includes a hardware processor and a storage that stores setting information on image associated information and a dynamic analysis including dynamic analyses. The image associated information is linked to the dynamic analysis among predetermined dynamic analyses of multiple types. The hardware processor acquires a dynamic image to be subject to the dynamic analysis and the image associated information of the dynamic image, specifies a type of the dynamic analysis that is applied to the dynamic image based on the acquired image associated information and the setting information stored in the storage, executes the dynamic analysis of the specified type to generate an analysis result, and outputs the generated analysis result.

9 Claims, 4 Drawing Sheets

(56) References Cited

U.S. PATENT DOCUMENTS

2020/0104994 A1*  4/2020  Sharma ................ G06T 11/003
2023/0230243 A1*  7/2023  Sun ...................... G06T 7/0012
                                                382/128

OTHER PUBLICATIONS

JPO Notice of Reasons for Refusal for corresponding JP Application No. 2021-048748; Issued Mar. 18, 2025.

* cited by examiner

| Setting No. | Associated Information | | | Analysis/Output Destination | | | | | | | | | | | | |
|---|---|---|---|---|---|---|---|---|---|---|---|---|---|---|---|---|
| | Region | Direction | Department | Ventilation | | Blood Flow | | Rib Removal | | Diaphragm Movement Amount | | Lung Tissue Highlight | | Adhesion/Wet Detection | | Image |
| | | | | Analysis | Output Destination | Analysis | Output Destination | Analysis | Output Destination | Analysis | Output Destination | Analysis | Output Destination | Analysis | Output Destination | Output Destination |
| 1 | Chest | Front | Respiratory Medicine | No | – | Yes | Image Storage Device | Yes | No | No | – | No | – | No | – | – |
| 2 | Chest | Front | Chest Surgery | Yes | Image Storage Device | No | – | No | – | No | – | No | – | No | – | – |
| 3 | Chest | Front | Emergency | Yes | Image Transmission Device | Yes | Image Transmission Device | Yes | Image Transmission Device | Yes | Image Transmission Device | Yes | Image Transmission Device | Yes | Image Transmission Device | – |
| ... | | | | | | | | | | | | | | | | |

DYNAMIC ANALYSIS DEVICE AND STORAGE MEDIUM

CROSS-REFERENCE TO RELATED APPLICATIONS

The present invention claims priority under 35 U.S.C. § 119 to Japanese Patent Application No. 2021-048748 filed on Mar. 23, 2021, the entire contents of which being incorporated herein by reference.

BACKGROUND

Technological Field

The present invention relates to a dynamic analysis device and a storage medium.

Description of the Related Art

In recent years, it has become possible for a radiographic imaging device to capture and acquire a dynamic image that shows dynamics of a subject. Dynamic images have more information in the time direction in comparison to conventional static images, and can provide more information to technicians and clinicians. For example, in diagnosis of the chest field, analyses of changes over time in a dynamic image of the chest can provide various kinds of information such as blood flow, ventilation, diaphragm movement amount, maximum ventilation, and the like as analysis results.

On the other hand, since there may be multiple types of analysis results that can be generated from one dynamic image, the time required for diagnosis of one patient may be increased problematically, as the information to be checked by a doctor in diagnosis increases.

Therefore, for example, JP2020081280A discloses a technique in which data of at least one of a static image, a dynamic image, an analysis result acquired by an analysis of the dynamic image by a data analysis means is automatically selected in view of checking the data and provided to a display device used by a doctor and the like.

Also, for example, JP2017205187A discloses a technique in which an analysis device executes analysis processing according to the type(s) of the dynamic analysis (analyses) included in imaging order information to provide the result(s) to a display device used by doctors and technicians.

SUMMARY

However, in JP2020081280A, since an image(s) necessary for diagnosis is selected according to the checking purpose after the data analysis means analyzes the dynamic image to generate the analysis result data, the analysis processing requires time and more storage amount.

In JP 2017205187A, though the type of analysis is included in the imaging order information, different analysis results may be required in different departments or at different phases of examination/treatment even when the same region is imaged. Therefore, the process of checking the required types of analyses and manually specifying the types of imaging in the imaging order information is troublesome and may lead to an error.

The present invention has been conceived in view of the above problems, and has an object of making it possible to generate an analysis result of a necessary dynamic analysis without the user manually specifying a type of dynamic analysis.

To achieve at least one of the abovementioned objects, a dynamic analysis device reflecting an aspect of the present invention includes:
    a hardware processor; and
    a storage that stores setting information on image associated information and a dynamic analysis,
    wherein the dynamic analysis includes multiple dynamic analyses;
    wherein the image associated information is linked to the dynamic analysis among predetermined dynamic analyses of multiple types,
    wherein the hardware processor:
        acquires a dynamic image to be subject to the dynamic analysis and the image associated information of the dynamic image;
        specifies a type of the dynamic analysis that is applied to the dynamic image based on the acquired image associated information and the setting information stored in the storage;
        executes the dynamic analysis of the specified type to generate an analysis result; and
        outputs the generated analysis result.

To achieve at least one of the abovementioned objects, a storage medium reflecting another aspect of the present invention causes a computer to:
    store setting information on image associated information and a dynamic analysis;
        wherein the dynamic analysis includes multiple dynamic analyses;
        wherein the image associated information is linked to the dynamic analysis among predetermined dynamic analyses of multiple types,
    acquire a dynamic image to be subject to the dynamic analysis and the image associated information of the dynamic image;
    specify a type of the dynamic analysis that is applied to the dynamic image based on the acquired image associated information and the setting information stored in the storage;
    execute the dynamic analysis of the specified type to generate an analysis result; and
    output the generated analysis result.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention, wherein.

DETAILED DESCRIPTION OF THE EMBODIMENTS

Hereinafter, one or more embodiments of the present invention are described with reference to the drawings.

However, the scope of the present invention is not limited to the embodiments or illustrated examples.

[Configuration of Dynamic Analysis System 100]

First, a configuration of an embodiment of the present invention is described.

Figure 1:
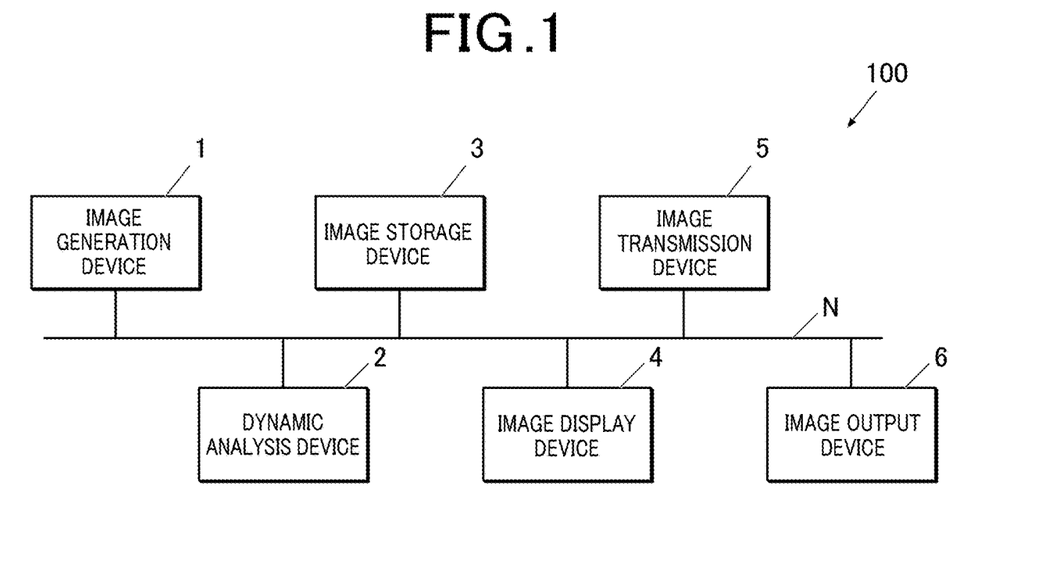
FIG. 1 shows an overall configuration of a dynamic analysis system in an embodiment of the present invention.

FIG. 1 shows a system configuration of a dynamic analysis system 100 in this embodiment.

As shown in FIG. 1, the dynamic analysis system 100 includes an image generation device 1, a dynamic analysis device 2, an image storage device 3, an image display device 4, an image transmission device 5, and image output device 6. These devices 1 to 5 are connected to each other to send and receive data to and from each other via a communication network N such as a LAN (local area network) built in a medical facility. The numbers of the devices are not particularly limited.

The image generation device 1 is a modality that images a subject region of a human body and generates digital data of the taken image. In this embodiment, the image generation device 1 is a radiographic imaging device that can generate a dynamic image by dynamic imaging of a subject with radiation. Dynamic imaging is performed by repeatedly emitting pulsed radiation, such as X-rays, to a subject at predetermined time intervals (pulse emission) or continuously emitting radiation without a break to a subject M at a low dose rate (continuous emission), thereby obtaining a plurality of images showing the dynamic state of the subject. A series of images obtained by dynamic imaging is called a dynamic image. A dynamic image includes a movie, but does not include a static image taken while a movie is being displayed. Images constituting a dynamic image are called frame images.

The image generation device 1 is a device in conformity with DICOM (Digital Imaging and Communications in Medicine) standard, and may receive external input of various kinds of information associated with a generated dynamic image (image associated information, hereinafter referred to as associated information), or, for example, may automatically generate associated information based on an imaging order sent from HIS (Hospital Information System), an RIS (Radiology Information System), or the like not shown in the drawings. The associated information includes, for example, patient information (patient ID, patient name, sex, date of birth), examination information (in addition to examination ID, examination date, examination time, at least one of: imaged region, imaging direction, modality type, image processing state (classification of done/yet to be done), number of frames, frame rate, movement information, medical department, diagnostician name, and phase of examination/treatment). Movement information, which is information on movement of a subject during imaging, includes a breathing state (breath-hold, deep breathing, resting breathing) for the chest (imaged region), and a bending state, a stretching state, or a rotation direction for an orthopaedic body part. The image generation device 1 adds the above-described associated information, UID (unique ID) for identifying an image, and the like as header information and sends them to the dynamic analysis device 2 via the communication network N.

The dynamic analysis device 2 is a computer device that generates an analysis result by performing a dynamic analysis of a dynamic image received from the image generation device 1 and outputs the generated analysis result. Here, a dynamic analysis means analysis processing performed on a dynamic image, and includes processing of enhancing or diminishing (removing) a predetermined structure by analyzing the dynamic image, as well as processing of analyzing movements of the subject based on a dynamic image.

Figure 2:
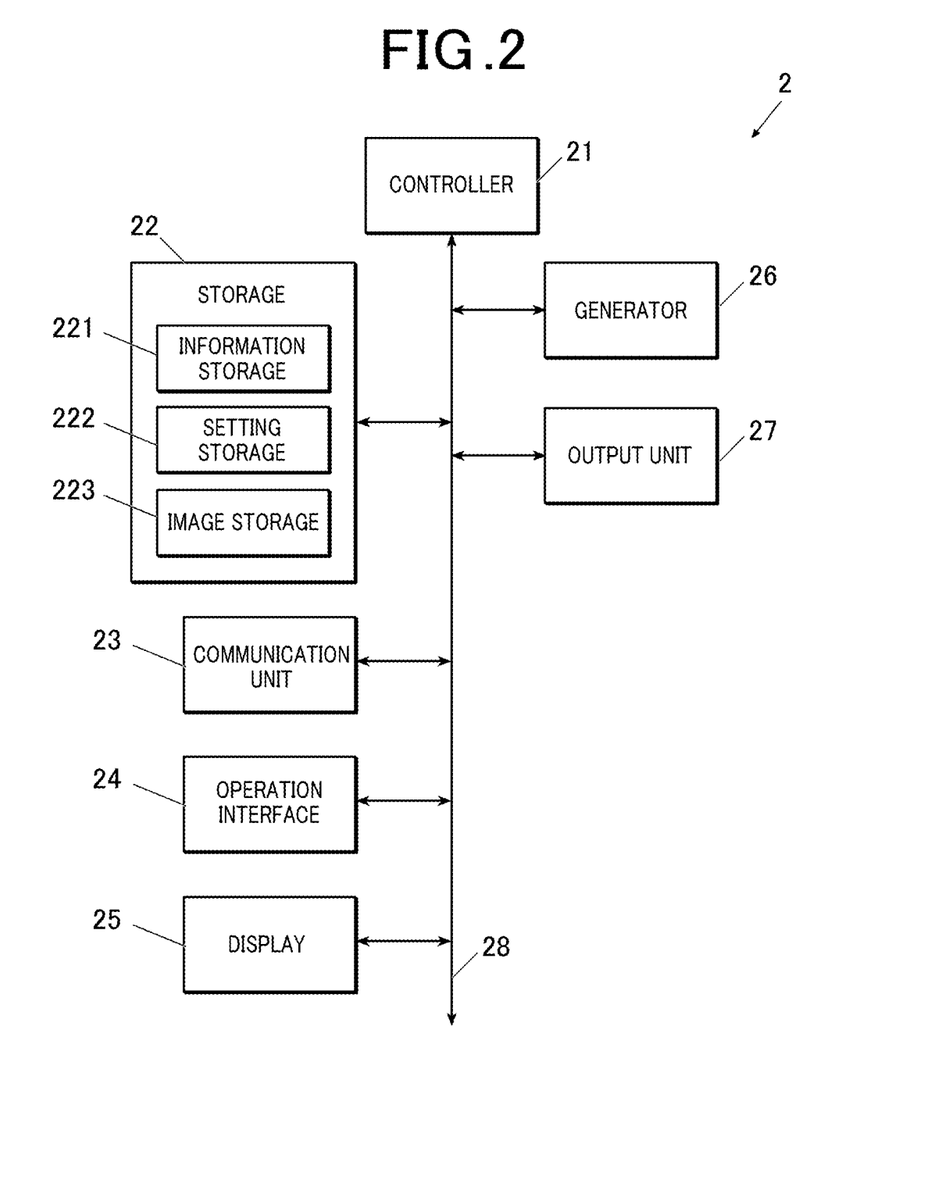
FIG. 2 is a block diagram showing a functional configuration of the dynamic analysis device in FIG. 1.

The dynamic analysis device 2 includes, as shown in FIG. 2, a controller 21 (hardware processor), a storage 22, a communication unit 23, an operation interface 24, a display 25, a generator 26 (hardware processor), and an output unit 27 (hardware processor), and these components are connected to each other via a bus 28.

The controller 21 includes a CPU (central processing unit) and a RAM (random access memory). The CPU of the controller 21 reads out a system program and various processing programs stored in the storage 22, loads them into the RAM, and controls the operations of the components of the dynamic analysis device 2 according to the loaded programs. For example, the controller 21 executes analysis control processing in cooperation with the program(s) stored in the storage 22 to control the operations of the components of the dynamic analysis device 2 in a dynamic analysis sequence shown in FIG. 4.

The storage 22 includes a non-volatile semiconductor memory and a hard disk. The storage 22 stores therein various programs to be executed by the controller 21, parameters necessary to execute processing of the programs, and data such as processing results, and the like. The programs are stored in a form of readable program code, and the controller 21 sequentially executes the operations according to the program code.

The storage 22 includes an information storage 221, a setting storage 222, and an image storage 223.

The information storage 221 is an area for temporarily storing dynamic images and associated information received from the image generation device 1, analysis results generated by the generator 26, and the like.

Figure 3:
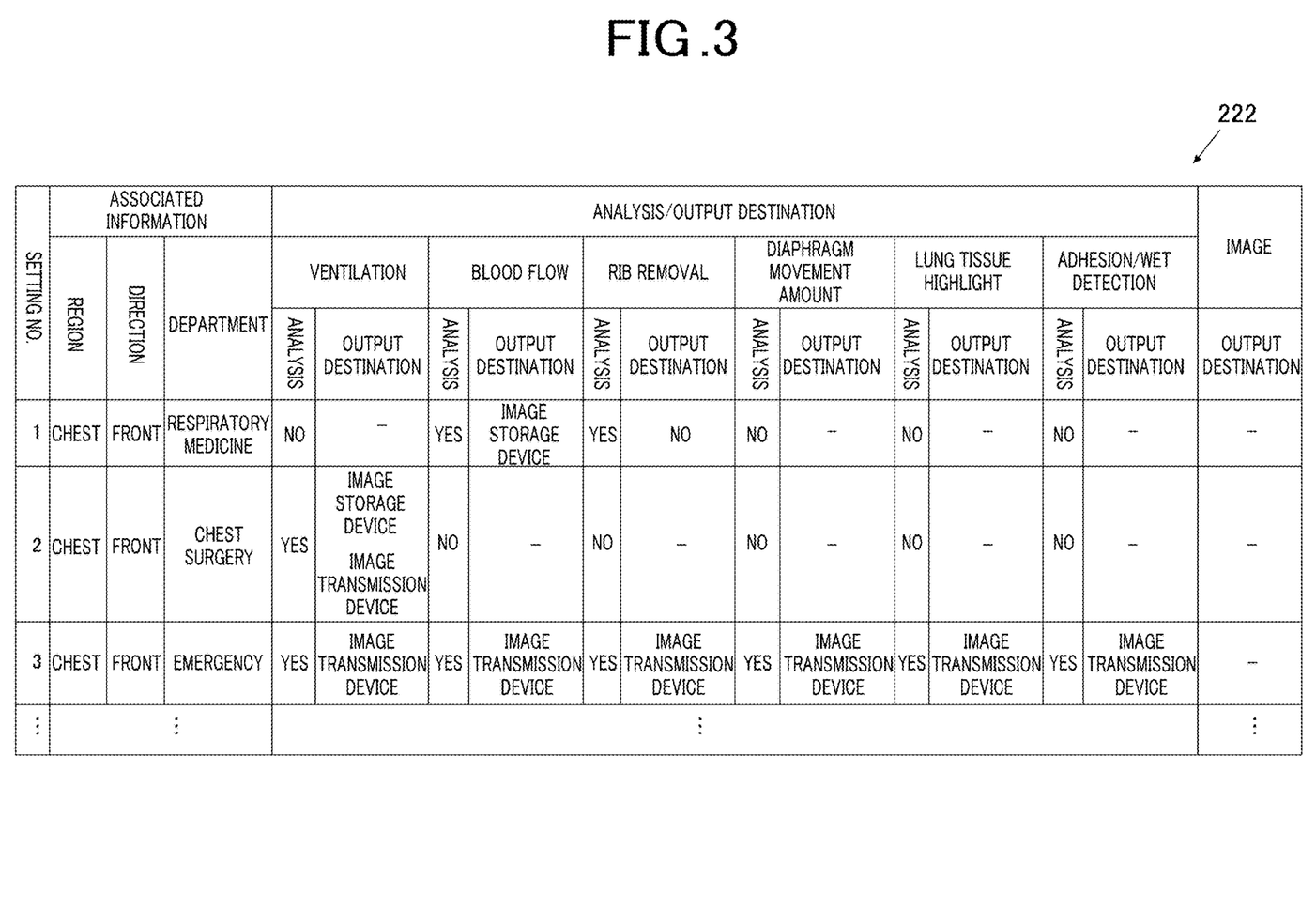
FIG. 3 shows an example of data storage in a setting storage.

The setting storage 222 is an area for storing setting information including associated information linked to one or more dynamic analyses from multiple kinds of dynamic analyses executable by the dynamic analysis device 2 and an output destination(s) of an analysis result(s). FIG. 3 shows an example of data storage of setting information in the setting storage 222. In FIG. 3, a dynamic analysis with "YES" in the "ANALYSIS" column is linked to the associated information in the same row among the multiple kinds of dynamic analyses executable by the dynamic analysis device 2 (e.g., ventilation analysis, blood flow analysis, rib removal, diaphragm movement amount). Since an analysis result is not generated for a dynamic analysis with "NO" in the "ANALYSIS" column, an "OUTPUT DESTINATION" of the concerning dynamic analysis cannot be set. Multiple output destinations may be set for a dynamic analysis with "YES" in the "ANALYSIS" column. Output destinations may include the image storage 223 and the display 25 of the dynamic analysis device 2, as well as the image storage device 3, the image display device 4, the image transmission device 5, and the image output device 6 which are external devices connected via the network N. Therefore, the analysis results may be viewed on the dynamic analysis device 2.

In FIG. 3, the items of the associated information are a region (imaged region), a direction (imaging direction), and a department, but are not limited to these examples. At least one of an imaged region, an imaging direction, a modality type, a processing state (done/not yet), a number of frames, a frame rate, movement information, a medical department, and a phase of examination/treatment may be set. The dynamic analyses (types of dynamic analyses) that can be set are not limited to the examples shown in FIG. 3. In this embodiment, an output destination of a dynamic image may be linked to the associated information. The associated information that does not require a dynamic analysis may be linked to an output destination of the dynamic image only, and in that case, the dynamic image may be output to the output destination without dynamic analysis.

The setting information stored in the setting storage 222 may be set via a setting screen (not shown in the drawings) shown on the display 25. The setting screen is a screen for setting the setting information to be stored in the setting storage 222, and when the user sets the content of the associated information via the operation interface 24 and sets a dynamic analysis to be linked to the associated information among the predetermined types of dynamic analyses and an output destination, the controller 21 stores the setting information including the set associated information linked to the set dynamic analysis and output destination in the setting storage 222.

On the setting screen, when the associated information of the setting information is set (input), a dynamic analysis that cannot be executed on the dynamic image corresponding to the associated information cannot be linked to the concerning associated information (setting is prohibited). For example, in the case where analyses of: ventilation; blood flow; rib removal; diaphragm movement amount; lung tissue enhancement; and adhesion/wet detection are executable in the dynamic analysis device 2, when any part other than the chest is set as the imaged region or any other direction than the front is set as the imaging direction in the associated information on the setting screen, any dynamic analyses mentioned above cannot be executed on the dynamic image corresponding to the set associated information, and therefore the controller 21 prohibits all the dynamic analyses from being linked to the concerning associated information. When the chest is set as the imaged region and the front as the imaging direction, and a modality type for a static image as the modality type in the associated information, any dynamic analyses other than rib removal is inexecutable on a static image, and therefore the controller 21 prohibits the dynamic analyses other than rib removal from being linked to the concerning associated information.

The image storage 223 is a database for storing the associated information of a dynamic image received from the image generation device 1 linked to the dynamic image and the analysis result(s).

The information storage 221, the setting storage 222, and the image storage 223 may be constituted of a common memory, hard disk or the like, or may be constituted of different memories, hard disks, or the like.

The communication unit 23 includes a LAN adapter, and controls data exchange with an external device(s) connected to the communication network N.

The operation interface 24 includes a keyboard including a cursor key, numeral input keys, and various function keys, and a pointing device such as a mouse. The operation interface 24 outputs, to the controller 21, an instruction signal which was input by a key operation to the keyboard and a mouse operation performed by the user. The operation interface 24 may include a touch panel on the display screen of the display 25. In this case, the operation interface 13 outputs an instruction signal input via the touch panel to the controller 21.

The display 25 is constituted of a monitor such as an LCD (liquid crystal display), and displays various contents according to commands of display signals input from the controller 21.

The generator 26 performs dynamic analyses on a dynamic image to generate analysis results. The analysis results include an analysis result image, a dynamic or static image with information to be emphasized being highlighted, numerical information calculated from the dynamic image, and graphs.

The generator 26 may be realized by the CPU of the controller 21 in cooperation with the program(s) stored in the storage 22, or by a hardware provided separately from the controller 21.

The output unit 27 outputs analysis results generated by the generator 26 to an output destination determined by the controller 21. The output unit 27 may be realized by the CPU of the controller 21 in cooperation with the program(s) stored in the storage 22, or by a hardware provided separately from the controller 21.

The image storage device 3 is, for example, a server of PACS (Picture Archiving and Communication System) or the like, and it is a device that includes an image database and that stores medical images such as a taken dynamic image and its analysis results associated with patient information and examination information in the image database.

The image display device 4 is a device for displaying medical images such as dynamic images and analysis results for doctors and the like to view them.

The image transmission device 5 is, for example, a Web (World Wide Web) server, and it is a device that generates a Web screen that allows medical images such as dynamic images and analysis results to be viewed on a Web browser and that provides data of the Web screen in response to an access via the Web browser.

The image output device 6 is a device that prints out a medical image on a film or paper sheet.

[Operations of Dynamic Analysis System 100]

Next, the operations of the dynamic analysis system 100 in this embodiment are described.

Figure 4:
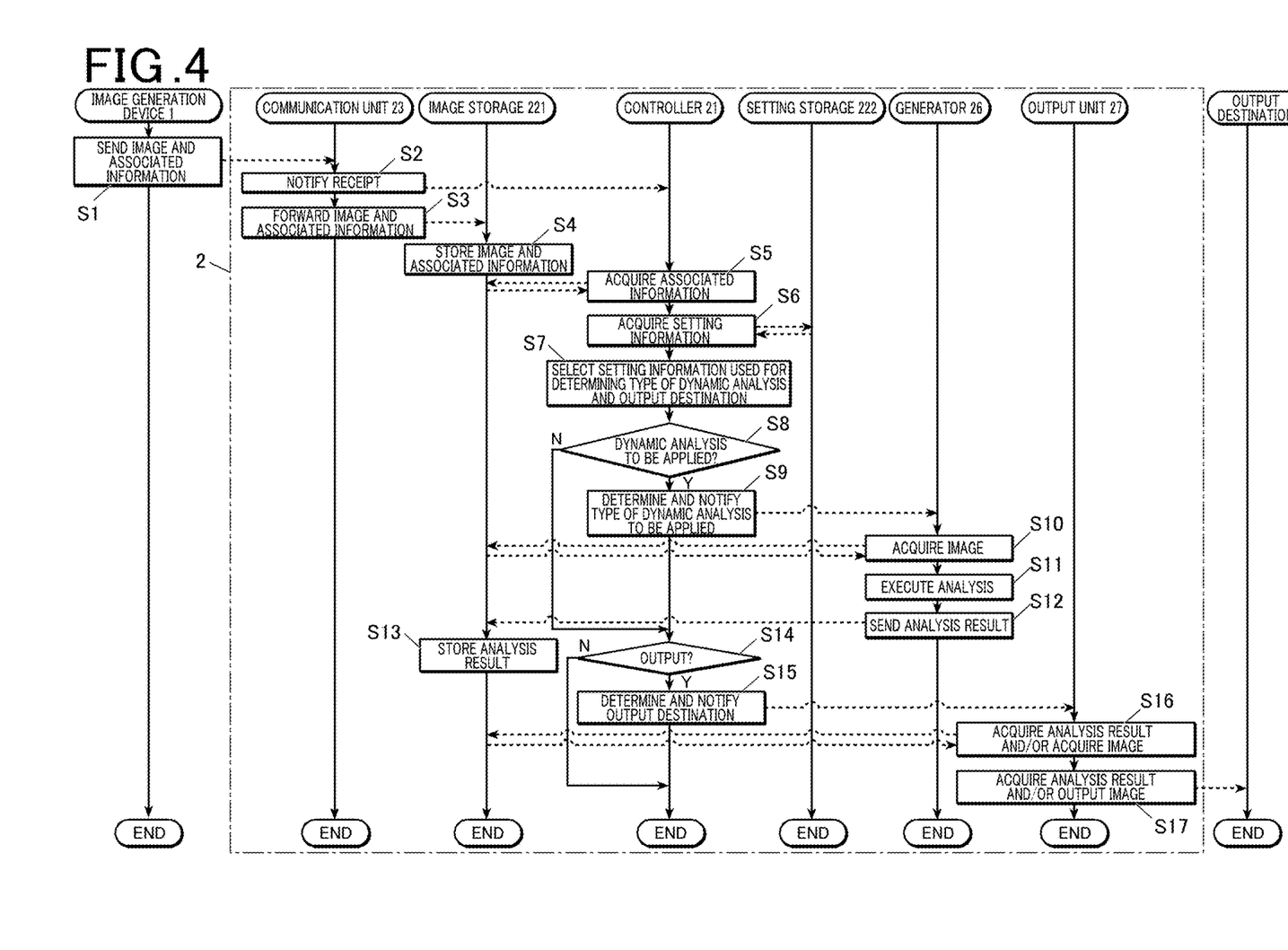
FIG. 4 shows a flow of a dynamic analysis sequence executed in the dynamic analysis system in FIG. 1.

FIG. 4 shows a dynamic analysis sequence executed after a dynamic image with associated information is generated in the image generation device 1. Hereinafter, the dynamic analysis sequence is described with reference to FIG. 4.

First, the image generation device 1 sends a dynamic image and its associated information to the dynamic analysis device 2 (Step S1).

Upon receipt of the dynamic image with the associated information sent from the image generation device 1, the communication unit 23 of the dynamic analysis device 2 notifies the controller 21 of the receipt (Step S2), and forwards the received dynamic image with the associated information to the information storage 221 (Step S3).

The information storage 221 stores the dynamic image with associated information forwarded from the communication unit 23 (Step S4).

When the communication unit 23 receives the dynamic information and the associated information from the image generation device 1, the controller 21 starts analysis control processing and controls the processing through Steps S5 to S17 in the dynamic analysis sequence to be executed.

First, the controller 21 acquires the received associated information from the information storage 221 (Step S5) and also acquires the setting information stored in the setting storage 222 (Step S6).

In this embodiment, the associated information is generated in the image generation device 1. However, the associated information may be information on an imaging order sent from HIS, RIS, or the like not shown in the drawings, or the associated information generated in the image generation device 1 and the information on the imaging order may be combined together to form the associated information.

In a case where the received dynamic image does not have any associated information or does not include necessary items of associated information, the controller 21 may calculate image feature values by a dynamic analysis and acquire information corresponding to the associated information (e.g., imaged region, imaging direction, modality type, movement information) based on the calculated image feature values. In that case, in order to make it easier to extract the image feature values, the subject may be imaged including a marker (radiopaque marker) at the time of imaging, or information marker that corresponds to the associated information may be added to the dynamic image by the console or the like of the image generation device 1. Alternatively, the state of the subject may be imaged with an optical camera separately at the time of imaging so that the controller 21 can acquire information corresponding to the associated information by analyzing the taken optical image.

Next, the controller 21 checks the acquired associated information and the setting information and selects the setting information used to specify the type of the dynamic analysis applied to the received dynamic image and the output destination (Step S7).

For example, the controller 21 sequentially checks the acquired associated information of the dynamic image and the setting information in the setting storage 222, and, if the setting information corresponding to the acquired associated information is stored, selects the concerning setting information as the setting information used to specify the dynamic analysis and the output destination.

Next, the controller 21 determines whether there is a dynamic analysis to be applied to the received dynamic image based on the selected setting information (Step S8).

If there is a dynamic analysis linked to the associated information in the selected setting information, the controller 21 determines that there is a dynamic analysis to be applied to the received dynamic image, and if there is no dynamic analysis linked to the associated information in the selected setting information, the controller 21 determines that there is no dynamic analysis to be applied to the received dynamic image.

If the controller 21 determines that there is a dynamic analysis to be applied to the received dynamic image (Step S8; Y), the controller 21 specifies that the type of the dynamic analysis linked to the associated information in the selected setting information is the type of the dynamic analysis to be applied to the received dynamic image, notifies the generator 26 of the specified type of the dynamic analysis, commands execution of the dynamic analysis (Step S9), and moves to Step S14.

If there are two or more items of the setting information corresponding to the acquired associated information, the controller 21 may specify the types of the dynamic analyses to be applied to the received dynamic image with logical sum or logical conjunction of the concerning items of the setting information. Alternatively, priority levels may be set for the setting information in advance to specify the type of the dynamic analysis to be applied based on the setting information with a higher priority level.

When the generator 26 is notified of the type of the dynamic analysis to be applied to the dynamic image and execution of the dynamic analysis is commanded by the controller 21, the generator 26 acquires the dynamic image to be analyzed from the information storage 221 (Step S10), and performs the dynamic analysis of the notified type to generate an analysis result (Step S11).

At Step S11, a parameter(s) used in the dynamic analysis (e.g., framerate) may be acquired from the associated information of the dynamic image and used.

When generation of the analysis result is complete, the generator 26 sends the analysis result to the information storage 221 (Step S12).

The information storage 221 stores the analysis result received from the generator 26 (Step S13).

If the controller 21 determines that there is no dynamic analysis to be applied to the received dynamic image at Step S8 (Step S8; N), the controller 21 moves to Step S14.

At Step S14, the controller 21 determines whether the analysis result and the dynamic image are to be output based on the setting information selected at Step S7 (Step S14).

If an output destination(s) of the analysis result of the applied dynamic analysis is specified in the setting information selected at Step S7, the controller 21 determines that the analysis result is to be output. If an output destination(s) of the dynamic image is specified in the selected setting information, the controller 21 determines that the dynamic image is to be output.

If the controller 21 determines that the analysis result or the dynamic image is to be output (Step S14; Y), the controller 21 specifies the output destination of the analysis result of the dynamic analysis applied to the dynamic image and/or the output destination of the dynamic image based on the setting information selected at Step S7, notifies the output unit 27 of the specified output destinations, and commands output of the analysis result and/or the dynamic image (Step S15).

When the output unit 27 is notified of the output destination of the analysis result and/or the dynamic image and output of the analysis result and/or the dynamic image is commanded by the controller 21, the output unit 27 acquires the analysis result and/or the dynamic image from the information storage 221 (Step S16). The output unit 27 then outputs the acquired analysis result and/or dynamic image to the output destination notified by the controller 21 (Step S17), and the dynamic analysis sequence is ended.

Here, if the output destination is an external device (e.g., the image storage device 3, the image display device 4, the image transmission device 5, the image output device 6), the output unit 27 causes the communication unit 23 to transmit the acquired analysis result and/or dynamic image to the external device. If the output destination is the image storage 223 of the dynamic analysis device 2, the output unit 27 outputs the acquired analysis result and/or dynamic image to the image storage 223 to be stored therein. If the output destination is the display 25 of the dynamic analysis device 2, the output unit 27 outputs the acquired analysis result and/or dynamic image to the display 25 to be displayed thereon. If the analysis result to be displayed is a dynamic image (an analysis result moving image or a dynamic image processed for enhancement), the framerate at which the result is to be played may be calculated from the associated information in the display 25 so that the result may be played at an appropriate framerate.

On contrary, if the controller 21 determines that the analysis result and the dynamic image are not to be output (Step S14; N), the dynamic analysis sequence is ended.

After the end of the dynamic analysis sequence, the controller 21 deletes the image, the associated information, and the analysis result concerning the received dynamic image that are stored temporarily in the information storage 221.

As described hereinbefore, the dynamic analysis device 2 includes the setting storage 222 storing the setting information in which associated information and a dynamic analysis (or dynamic analyses) among dynamic analyses of multiple predetermined types are linked, and upon receipt of the dynamic image subject to the dynamic analysis and the associated information concerning the dynamic image via the communication unit 23, the controller 21 specifies the type of the dynamic analysis to be applied to the dynamic image based on the associated information of the received dynamic image and the setting information stored in the setting storage 222, and the generator 26 performs the dynamic analysis of the specified type on the dynamic image to generate an analysis result. The output unit 27 then outputs the generated analysis result.

Therefore, it is possible to generate a necessary dynamic analysis result only without specifying the type of dynamic analysis.

The associated information includes an output destination of the analysis result of the dynamic analysis linked to the concerning associated information in the setting information, and the controller 21 specifies the output destination of the generated analysis result based on the received associated information and the setting information stored in the setting storage 222 and the output unit 27 outputs the analysis result to the specified output destination.

Therefore, it is possible to output the dynamic analysis result to a necessary output destination without manually specifying the output destination.

It is also possible to set setting information as the user needs because the setting information can be set in the setting storage 222 via the setting screen.

It is also possible to prevent the dynamic analysis inexecutable on the image from being executed because the controller 21 prohibits a dynamic analysis inexecutable on a dynamic image from being set as a dynamic analysis linked to the set image associated information.

For example, in the case where one or more of ventilation analysis, blood flow analysis, rib removal, diaphragm movement amount, lung tissue enhancement, and adhesion/wet detection is settable as a dynamic analysis, when any region other than the chest is set as the imaged region in the associated information or when any direction other than the front is set as the imaging direction, the controller 21 prohibits all the types of the dynamic analyses from being linked to the associated information in the setting information. When the chest is set as the imaged region, the front as the imaging direction, a modality for static imaging as the modality type, the controller 21 prohibits any dynamic analysis other than the rib removal from being linked to the associated information in the setting information. Therefore, it is possible to prevent a dynamic analysis inexecutable on the image from being executed.

The description in the above-described embodiment is a preferred example of the present invention, and does not limit the present invention.

For example, in the above-described embodiment, the image transmission device 5 is an external device, but the dynamic analysis device 2 may include functions as an image transmission device (e.g. a function to generate a Web screen that allows medical images such as dynamic images and analysis results to be viewed on a Web browser and provides the data of the Web screen in response to an access via the Web browser) therein to set the image transmission device inside the dynamic analysis device and output analysis results or dynamic images to the image transmission device inside the dynamic analysis device 2.

In the above-described embodiment, the present invention is applied when a dynamic analysis is executed on a dynamic image received and acquired from the image generation device 1 in the dynamic analysis device 2, but the present invention is not limited to this example. For example, the present invention may be applied when a dynamic analysis is executed on a dynamic image specified by the user from dynamic images stored in the image storage 223 and acquired from the image storage 223.

When multiple analysis results are output from a static image as well as a dynamic image, only necessary analysis results may be output referring to the associated information of the image and the setting information stored in the setting storage 222, as in the above-described embodiment.

In the above-described embodiment, the present invention is applied to the dynamic analysis device 2 that performs dynamic analyses on dynamic images acquired from the image generation device 1 of one medical facility to output analysis results. However, the present invention may be applied to a server device that performs dynamic analyses on dynamic images acquired (received) from multiple medical facilities to output analysis results to the medical facilities that send the dynamic images.

The above description discloses an example of using a hard disk or semiconductor non-volatile memory as a computer-readable medium for the program, but the invention is not limited to this example. A portable recording medium such as a CD-ROM can be applied as other computer readable mediums. A carrier wave is also applied as a medium providing the program data according to the present invention via a communication line.

In addition to the above, detailed configurations and detailed actions of the components of the dynamic analysis system can also be appropriately modified without departing from the spirit of the present invention.

What is claimed is:

1. A dynamic analysis device comprising:
   a hardware processor; and
   a storage that stores setting information on image associated information and a dynamic analysis,
   wherein the dynamic analysis includes multiple dynamic analyses;
   wherein the image associated information is linked to the dynamic analysis among predetermined dynamic analyses of multiple types,
   wherein the hardware processor:
      acquires a dynamic image to be subject to the dynamic analysis and the image associated information of the dynamic image;
      specifies a type of the dynamic analysis that is applied to the dynamic image based on the acquired image associated information and the setting information stored in the storage;
      executes the dynamic analysis of the specified type to generate an analysis result; and
      outputs the generated analysis result;
   wherein the dynamic analysis is specified based on one or more of an imaged region and an imaging direction of an image generation device relative to an imaging subject.

2. The dynamic analysis device according to claim 1,
   wherein the image associated information includes one or more of: a number of frames; a frame rate; a modality type; a classification of whether image processing is done or not; an imaged region; an imaging direction; movement information; a medical department; a doctor name; and a diagnosis phase.

3. The dynamic analysis device according to claim 1,
wherein in the setting information, the image associated information is linked to an output destination of the analysis result of the dynamic analysis linked to the image associated information,
wherein the hardware processor specifies the output destination of the generated analysis result based on the acquired image associated information and the setting information stored in the storage,
wherein the hardware processor outputs the generated analysis result to the specified output destination.

4. The dynamic analysis device according to claim 3,
wherein the output destination includes one or more of an image storage in the dynamic analysis device, an image display, an image output device of an external device, an image storage device, an image display device, and an image transmission device.

5. The dynamic analysis device according to claim 1,
wherein the hardware processor sets the setting information in the storage.

6. The dynamic analysis device according to claim 5,
wherein the hardware processor prohibits a dynamic analysis inexecutable on the dynamic image corresponding to the set image associated information from being set as a dynamic analysis linked to the set image associated information.

7. The dynamic analysis device according to claim 5,
wherein one or more of a ventilation analysis, a blood flow analysis, a rib removal, a diaphragm movement amount, lung tissue enhancement, and adhesion/wet detection is settable as the dynamic analysis in the setting information,
wherein, for first image associated information in which any region other than a chest is set as an imaged region or in which any direction other than a front is set as an imaging direction, the hardware processor prohibits any of the multiple dynamic analyses from being linked to the first image associated information, and for second image associated information in which the chest is set as the imaged region, in which the front is set as the imaging direction, or in which a modality for a static image is set as a modality type, the hardware processor prohibits the dynamic analysis other than rib removal from being linked to the second image associated information.

8. A non-transitory storage medium storing a computer-readable program that causes a computer to:
store setting information on image associated information and a dynamic analysis;
wherein the dynamic analysis includes multiple dynamic analyses;
wherein the image associated information is linked to the dynamic analysis among predetermined dynamic analyses of multiple types,
acquire a dynamic image to be subject to the dynamic analysis and the image associated information of the dynamic image;
specify a type of the dynamic analysis that is applied to the dynamic image based on the acquired image associated information and the setting information stored in the storage;
execute the dynamic analysis of the specified type to generate an analysis result; and
output the generated analysis result;
wherein the dynamic analysis is specified based on one or more of an imaged region and an imaging direction of an image generation device relative to an imaging subject.

9. A dynamic analysis device comprising:
a hardware processor; and
a storage that stores setting information on image associated information and a dynamic analysis,
wherein the dynamic analysis includes multiple dynamic analyses;
wherein the image associated information is linked to the dynamic analysis among predetermined dynamic analyses of multiple types,
wherein the hardware processor:
acquires a dynamic image to be subject to the dynamic analysis and the image associated information of the dynamic image;
specifies a type of the dynamic analysis that is applied to the dynamic image based on the acquired image associated information and the setting information stored in the storage;
executes the dynamic analysis of the specified type to generate an analysis result; and
outputs the generated analysis result;
wherein the hardware processor sets the setting information in the storage;
wherein one or more of a ventilation analysis, a blood flow analysis, a rib removal, a diaphragm movement amount, lung tissue enhancement, and adhesion/wet detection is settable as the dynamic analysis in the setting information,
wherein, for first image associated information in which any region other than a chest is set as an imaged region or in which any direction other than a front is set as an imaging direction, the hardware processor prohibits any of the multiple dynamic analyses from being linked to the first image associated information, and for second image associated information in which the chest is set as the imaged region, in which the front is set as the imaging direction, or in which a modality for a static image is set as a modality type, the hardware processor prohibits the dynamic analysis other than rib removal from being linked to the second image associated information.

* * * * *